United States Patent
Lo et al.

(10) Patent No.: US 9,689,869 B2
(45) Date of Patent: *Jun. 27, 2017

(54) FLUORESCENCE EXCITATION DEVICE AND PORTABLE FLUORESCENCE ANALYSIS SYSTEM WITH THE SAME

(71) Applicant: National Tsing Hua University, Hsinchu (TW)

(72) Inventors: Shih-Jie Lo, Hsinchu (TW); Min-Wei Hung, Hsinchu (TW); Jer-Liang Yeh, Hsinchu (TW); Da-Jeng Yao, Hsinchu (TW); Chao-Min Cheng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/757,476

(22) Filed: Dec. 23, 2015

(65) Prior Publication Data
US 2016/0116465 A1 Apr. 28, 2016

Related U.S. Application Data

(63) Continuation of application No. 14/181,045, filed on Feb. 14, 2014, now Pat. No. 9,255,884.

(30) Foreign Application Priority Data
Nov. 19, 2013 (TW) .............................. 102142015 A

(51) Int. Cl.
*G01N 33/543* (2006.01)
*G01N 21/64* (2006.01)
(Continued)

(52) U.S. Cl.
CPC ....... *G01N 33/54366* (2013.01); *G01N 21/01* (2013.01); *G01N 21/645* (2013.01);
(Continued)

(58) Field of Classification Search
CPC ............... G01N 21/6486; G01N 21/01; G01N 33/54366; G01N 33/54306;
(Continued)

(56) References Cited

U.S. PATENT DOCUMENTS

2010/0135857 A1  6/2010  Hunter et al.
2010/0141153 A1*  6/2010  Recker ............... H05B 33/0803
                                                        315/149

FOREIGN PATENT DOCUMENTS

TW       M465672 U       11/2013

OTHER PUBLICATIONS

An Office Action from the corresponding Taiwanese application mailed Feb. 15, 2016 is attached, 19 pages.
(Continued)

*Primary Examiner* — David Porta
*Assistant Examiner* — Faye Boosalis
(74) *Attorney, Agent, or Firm* — Muncy, Geissler, Olds & Lowe, P.C.

(57) ABSTRACT

A portable fluorescence analysis system comprises a fluorescence strip, a fluorescence excitation device and a mobile Internet device. The fluorescence strip comprises a fluorescence probe configured for detecting an analyte within a specimen. The fluorescence excitation device comprises a sleeve and an excitation light source module. The fluorescence strip is arranged at the one open end of the sleeve. The excitation light source module is arranged at the same opening side of the sleeve and configured for providing an excitation light to excite the fluorescence probe to generate fluorescence. The mobile Internet device comprises an
(Continued)

image capturing module and configured for capturing a fluorescence image of the fluorescence strip via the other opening of the sleeve and analyzing fluorescence intensity of the fluorescence image to determine the content of the analyte. The above-mentioned system can be applied to the point of care testing.

35 Claims, 3 Drawing Sheets

(51) Int. Cl.
    *H05K 5/00*     (2006.01)
    *G01N 21/01*     (2006.01)
    *H04W 4/00*     (2009.01)

(52) U.S. Cl.
    CPC ..... *G01N 21/6456* (2013.01); *G01N 21/6486* (2013.01); *G01N 33/54306* (2013.01); *H04W 4/008* (2013.01); *H05K 5/0086* (2013.01); *G01N 2021/0137* (2013.01); *G01N 2021/6482* (2013.01); *G01N 2201/061* (2013.01); *G01N 2201/062* (2013.01)

(58) Field of Classification Search
    CPC ... G01N 2021/0137; G01N 2021/6482; G01N 21/6454; G01N 21/6456; G01N 2201/061
    See application file for complete search history.

(56) References Cited

OTHER PUBLICATIONS

An Office Action from the corresponding CN Application No. 201410050123.6 mailed Nov. 28, 2016, 10 pages.

* cited by examiner

FLUORESCENCE EXCITATION DEVICE AND PORTABLE FLUORESCENCE ANALYSIS SYSTEM WITH THE SAME

CROSS-REFERENCES TO RELATED APPLICATIONS

This application is a continuation application of U.S. Ser. No. 14/181,045, filed on Feb. 14, 2014, which claims the priority to Taiwan Patent Application No. 102142015.

This application claims the benefit of the priority to Taiwan Patent Application No. 102142015 filed on Nov. 19, 2013, the disclosures of which are incorporated herein by reference in their entirety.

BACKGROUND OF THE INVENTION

1. Field of the Invention

The present invention relates to a portable fluorescence analysis system, and more particularly to a fluorescence strip, a fluorescence excitation device and a portable fluorescence analysis system utilizing a mobile Internet device to capture fluorescence images.

2. Description of the Prior Art

The paper-based analysis device applied to clinical usage has been widely developed. For example, specific antigens, antibodies or nucleic acids can be monitored by the colorimetry or fluorescence signals. However, the colorimetry is limited by specific chemical reactions. While the sensibility and storage convenience of fluorescence strip are better than that of the colorimetry, such as the enzymatic analysis, the fluorescence analysis needs expensive and complex optical instruments. In this respect, the fluorescence analysis cannot be effectively and widely implemented to the field of the point of care testing (POCT). The point of care testing is not performed in the conventional laboratory but is performed at a location, such as a consulting room, an emergency room, a ward and a home environment, proximate to a patient. That is to say, the basic requirements for the point of care testing are economical, prompt and convenient.

According to the foregoing descriptions, the extremely desired goal to be achieved is to provide a portable fluorescence analysis system at the present time.

SUMMARY OF THE INVENTION

The present invention provides a fluorescence strip, a fluorescence excitation device and a portable fluorescence analysis system, and particularly to a fluorescence excitation device mounted to a mobile Internet device, such as a smart mobile phone or a tablet PC, and capturing a fluorescence image of fluorescence strip to be analyzed by the mobile Internet device. Hence, the portable fluorescence analysis system of this invention achieves the effects of being economical, prompt and convenient, and being adapted to the point of care testing.

In one embodiment, the proposed portable fluorescence analysis system comprises a fluorescence strip, a fluorescence excitation device and a mobile Internet device. The fluorescence strip comprises at least a detecting area, and the detecting area comprises a fluorescence probe for detecting an analyte within a specimen. The fluorescence excitation device comprises a sleeve and an excitation light source module. The sleeve is non-transparent and has a first opening and a second opening opposite to the first opening. The fluorescence strip is arranged to the side of the second opening of the sleeve. The excitation light source module is arranged to the side of the second opening for providing an exciting light irradiating on the detecting area of the fluorescence strip so as to excite the fluorescence probe to generate a fluorescent light. The mobile Internet device comprises an image capturing module and is arranged to the side of the first opening of the sleeve for capturing a fluorescence image of the detecting area via the first opening and analyzing a fluorescence intensity of the fluorescence image to estimate a content of the analyte.

In another embodiment, the proposed fluorescence excitation device forms a portable fluorescence analysis system with a fluorescence strip and a mobile Internet device. The fluorescence strip comprises at least one detecting area, and the detecting area comprises a fluorescence probe for detecting an analyte within a specimen. The mobile Internet device comprises an image capturing module. The fluorescence excitation device comprises a sleeve and an excitation light source module. The sleeve is non-transparent and has a first opening and a second opening opposite to the first opening, wherein the fluorescence strip is arranged to the side of the second opening of the sleeve. The excitation light source module is arranged to the side of the second opening for providing an exciting light irradiating on the detecting area so as to excite the fluorescence probe to generate a fluorescent light The image capturing module captures a fluorescence image of the detecting area via the first opening and analyzes a fluorescence intensity of the fluorescence image to estimate a content of the analyte.

In yet another embodiment, the proposed fluorescence strip forms a portable fluorescence analysis system with a fluorescence excitation device and a mobile Internet device, wherein the mobile Internet device comprises an image capturing module. The fluorescence strip comprises at least one detecting area and a focus area. The detecting area comprises a fluorescence probe. After the fluorescence probe is bonded or adhered with an analyte within a specimen, the fluorescence probe is excited by an exciting light emitted from the fluorescence excitation device to generate a fluorescent light for the mobile Internet device to capture a fluorescence image of the detecting area and analyze a fluorescence intensity of the fluorescence image to estimate a content of the analyte within the specimen. The focus area is configured for assisting the mobile Internet device to capture the fluorescence image in focus.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

The detailed explanation of the present invention is described as follows. The described preferred embodiments are presented for purposes of illustrations and description, and they are not intended to limit the scope of the present invention.

Figure 1:
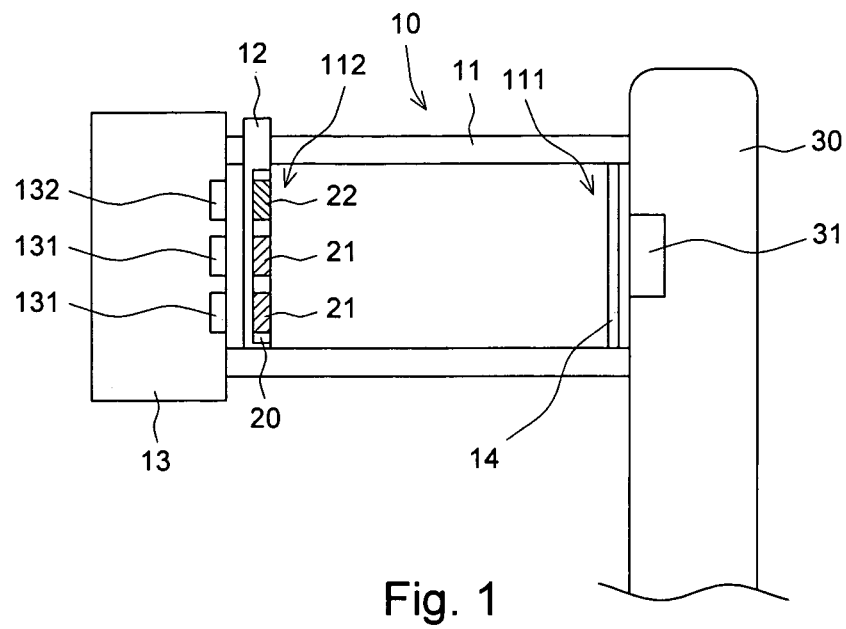
FIG. 1 is a schematic diagram schematically illustrating one embodiment of a portable fluorescence analysis system according to the present invention.
Figure 2A:
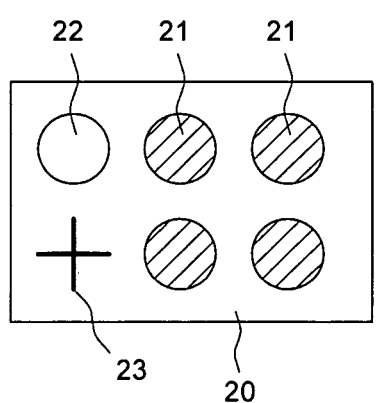
FIGS. 2a and 2b are schematic diagrams schematically illustrate one embodiment of a fluorescence strip of a portable fluorescence analysis system according to the present invention.
Figure 2B:
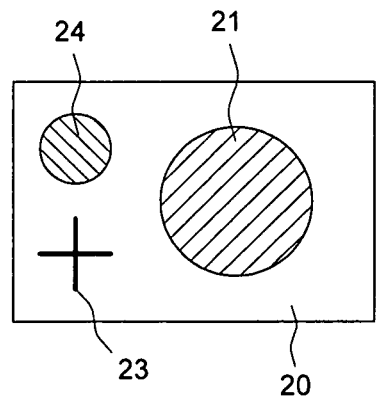

FIG. 1 shows one embodiment of the portable fluorescence analysis system of the present invention which comprises a fluorescence strip 20, a fluorescence excitation device 10 and a mobile Internet device 30. The fluorescence strip 20 comprises at least one detecting area 21 as shown in FIGS. 2a and 2b. The detecting area 21 has a fluorescence probe fixed therein and configured for detecting an analyte within a specimen, such as an antigen, an antibody, a nucleic acid or the like. It should be noted that one fluorescence strip 20 may comprise a single detecting area 21 (shown in FIG. 2b) or a plurality of detecting areas 21 (shown in FIG. 2a). In one embodiment, the fluorescence probe of any detecting area 21 in the fluorescence strip 20 comprising the plurality of detecting areas 21 may be the same or different. For example, if the plurality of detecting areas 21 comprise the same fluorescence probe, the fluorescence strip 20 is adapted to detect the same kind of analyte in different specimens or is adapted to detect the same kind of analyte in a single specimen repeatedly at the same time. If the plurality of detecting areas 21 comprise different fluorescence probes, the fluorescence strip 20 is adapted to detect a plurality of types of analytes in a single specimen at the same time. The fluorescence detection by utilizing paper substrates can be accomplished by the presently known fluorescence detecting techniques, thus it is not further described herein.

The fluorescence excitation device 10 comprises a sleeve 11 and an excitation light source module 13. The sleeve 11 may be a non-transparent material or is configured to block external lights entering the interior of the sleeve 11 in a proper manner. The sleeve 11 has a first opening 111 and a second opening 112 opposite to the first opening 111. In one embodiment, the fluorescence strip 20 is configured to be arranged directly at the end of the second opening 112 of the sleeve 11. Alternatively, the fluorescence excitation device 10 comprises a fixing member 12 arranged to the side of the second opening 112 of the sleeve 11. The fixing member 12 is configured to fix the fluorescence strip 20. The manner that the fixing member 12 is fixed to the fluorescence strip 20 is not limited. For example, a guide slot may be provided on the side of the second opening 112 of the sleeve 11, so that the fluorescence strip 20 is fixed to the sleeve 11 by directly inserting the fluorescence strip 20 into the guide slot. In this example, the fixing member 12 is the guide slot. Alternatively, the fluorescence strip 20 is firstly held by a holding member and then fixed to the sleeve 11 by inserting the holding member with the fluorescence strip 20 into the guide slot; in this example, the fixing member 12 comprises the guide slot and the holding member. The excitation light source module 13 is arranged to the side of the second opening 112 of the sleeve 11. The excitation light source module 13 provides an exciting light irradiating on the detecting area 21 of the fluorescence strip 20 so as to excite the fluorescence probe within the detecting area 21 to generate a fluorescent light. In one embodiment, the excitation light source module 13 comprises at least one LED 131 (Light Emitting Diode), and each detecting area 21 is corresponding to at least one LED 131. In one embodiment, the exciting light may be a UV-light, and the fluorescent light may be a visible light. In the embodiment as shown in FIG. 1, the excitation light source module 13 is arranged opposite to the mobile Internet device 30. That is to say, the fluorescence strip 20 is arranged between the excitation light source module 13 and the mobile Internet device 30. Nevertheless, the arrangement among the fluorescence strip 20, the excitation light source module 13 and the mobile Internet device 30 is not limited to the present embodiments. For example, under the situation without interfering with the mobile Internet device 30 to capture image, the excitation light source module 13 and the mobile Internet device 30 can be arranged at the same side relative to the fluorescence strip 20.

The mobile Internet device 30, such as a smart mobile phone or a tablet computer, comprises an image capturing module 31. The image capturing module 31 of the mobile Internet device 30 is aligned to the first opening 111 of the sleeve 11, so that the image capturing module 31 can capture the fluorescence light emitted from the fluorescence probe of the detecting area 21 via the first opening 111, and hence forming a fluorescence image. The content of analyte can be estimated by analyzing a fluorescence intensity of the fluorescence image. For example, a curve graph comprising a known relationship between the content of analyte and the fluorescence intensity can be made in advance, so that the content of analyte can be obtained by referring to the detected fluorescence intensity and the curve graph. It should be noted that the relationship between the content of analyte and the fluorescence intensity may be positive relationship or negative relationship. That is to say, when the content of analyte is higher, the fluorescence intensity may be higher or lower. In one embodiment, analyzing the fluorescence intensity within a specific wavelength range is preferred. For example, a fluorescent light may comprise different light wavelength ranges of the red light, the green light and the blue light, but the content of analyte may simply have a remarkable relevance with the red light. In this case, the follow-up analysis can simply focus on analyzing the light intensity within the wavelength of the red light.

In one embodiment, the fluorescence intensity of the fluorescence image is analyzed by an image processing software installed in the mobile Internet device 30. It is noted that, the manner for analyzing the fluorescence intensity of the fluorescence image is not limited. For example, arranging a relating image processing hardware in the mobile Internet device 30 can also achieve the same goal. Further, to lower calculating loadings for the mobile Internet device 30, the mobile Internet device 30 can transfer the fluorescence image to a host, such as a desktop computer or a remote server, to analyze the fluorescence image.

In general, the exciting light has a different light wavelength range from the fluorescent light. Referring to FIG. 1, to prevent the exciting light emitted from excitation light source module 13 from interfering the image to be captured by the image capturing module 31 of the mobile Internet device 30, a filter 14 can be arranged to the side of the first opening 111 of the sleeve 11. The filter 14 filters out the light within the wavelength ranges of the exciting light and allows the fluorescent light to pass through so as to prevent the exciting light from interfering the image to be captured and the corresponding analysis result. As the mentioned above, the content of the analyte may simply have a remarkable relevance with the light having a specific wavelength range.

Therefore, the filter 14 can concurrently filter out the exciting light and the light excluding a specific wavelength range of the fluorescent light so as to lower calculating loadings for the subsequent image processing.

In one embodiment, the interior surface of the sleeve 11 has a light absorbing layer (not shown). The light absorbing layer is adapted for absorbing the exciting light emitted from the excitation light source module 13 and/or the fluorescent light generated by the fluorescence strip 20, so that the lights reflected by the interior surface of the sleeve 11 is reduced and hence the quality of the fluorescence image is improved.

In general, when shooting or photographing within a close distance, the image capturing module 31 of the mobile Internet device 30 is not easy to focus. Referring to FIGS. 2a and 2b, to focus easily, a focus area is arranged on the fluorescence strip 20. For example, the focus area comprises a focus pattern 23. The focus pattern 23 assists the mobile Internet device 30 to focus so as to capture the fluorescence image in focus. For example, the focus pattern 23 comprises but not limited to a cross pattern and a stripe/checker pattern in black and white. In one embodiment, the focus pattern 23 comprises a fluorescence material, so that the focus pattern 23, under being excited, forms a fluorescence pattern to assists the image capturing module 31 to focus under the environment lacking of light source.

Referring to FIG. 2b, in one embodiment, the fluorescence strip 20 comprises at least a control area 24. The control area 24 comprises a known amount of fluorescence material, so that when the control area 24 is excited, the control area 24 generates a fluorescent light with steady fluorescence intensity. Based on the fluorescence intensity generated from the control area 24, the image capturing module 31 can adjust an exposure value so as to capture the fluorescence image in a proper exposure value. Further, when analyzing the fluorescence intensity of the fluorescence image, the fluorescence intensity of the control area 24 is adapted to be a compensation basis so as to obtain more accurate analysis result.

As shown in FIGS. 1 and 2a, in one embodiment, the excitation light source module 13 is further configured to provide a reference light, and the fluorescence strip 20 has a hole 22 corresponding to the reference light. Under this arrangement, the image capturing module 31 can adjust an exposure value based on light intensity of the reference light so as to capture the fluorescence image in a proper exposure value. To prevent the reference light from being filtered out by the filter 14, in one embodiment, the center wavelength of the reference light is different from that of the exciting light. For example, the LED 131 of the excitation light source module 13 emits exciting light to excite the fluorescence probe to generate fluorescent light. A LED 132 emits the reference light, and the image capturing module 31 senses the reference light via the hole 22 of the fluorescence strip 20 to adjust a exposure value. It is understood that when analyzing the fluorescence intensity of the fluorescence image, the area corresponding to the reference light is adapted to be a compensation basis so as to obtain more accurate analysis result.

Figure 3:
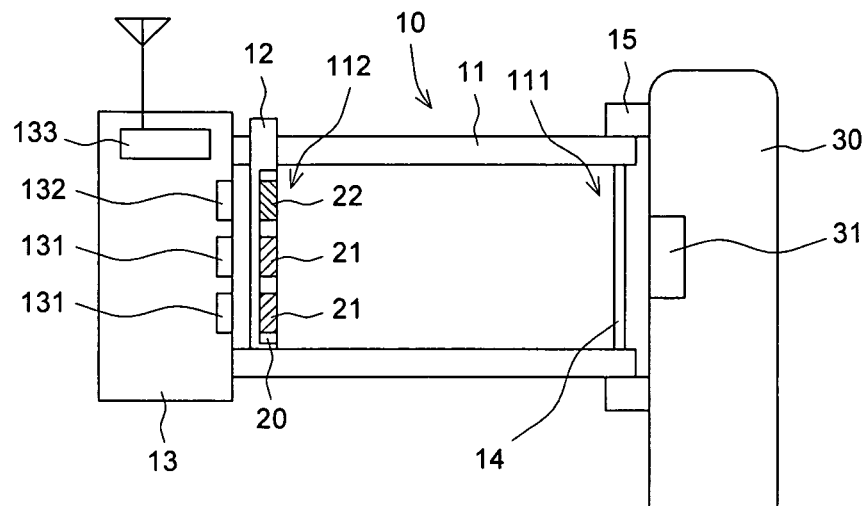
FIGS. 3 and 4 are schematic diagrams schematically illustrate another embodiment of a portable fluorescence analysis system according to the present invention.

As shown in FIG. 3, in one embodiment, the fluorescence excitation device 10 further comprises an adapter 15 arranged to the side of the first opening 111 of the sleeve 11. Under this arrangement, the fluorescence excitation device 10 is adapted to be installed on the mobile Internet devices 30 having different types or shapes based on selecting the proper adapter 15.

In one embodiment, the excitation light source module 13 further comprises a Bluetooth module 133. The Bluetooth module 133 enables the excitation light source module 13 and the mobile Internet device 30 to perform wireless communication. Therefore, a user can control the excitation light source module 13 through a user interface of the mobile Internet device 30. For example, through a user interface of the mobile Internet device 30, a user can adjust the intensity of the exciting light emitted from the excitation light source module 13 or selectively activate at least one of a plurality of LEDs 131.

Figure 4:
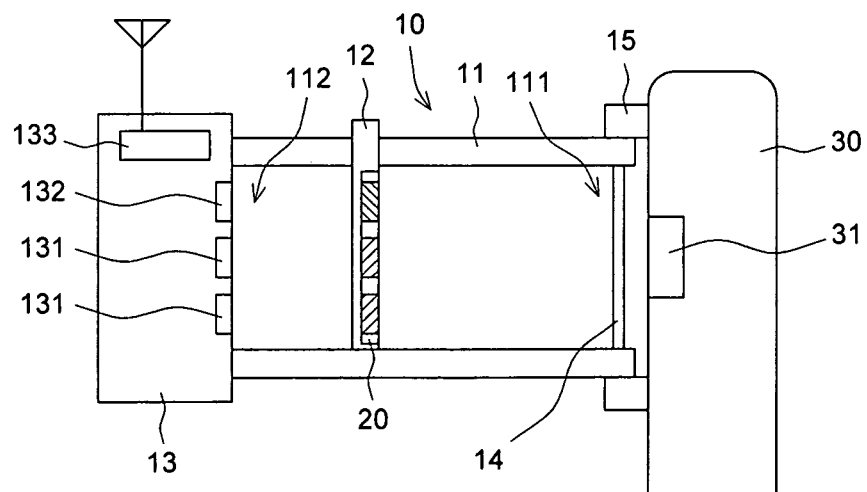
Figure 5A:
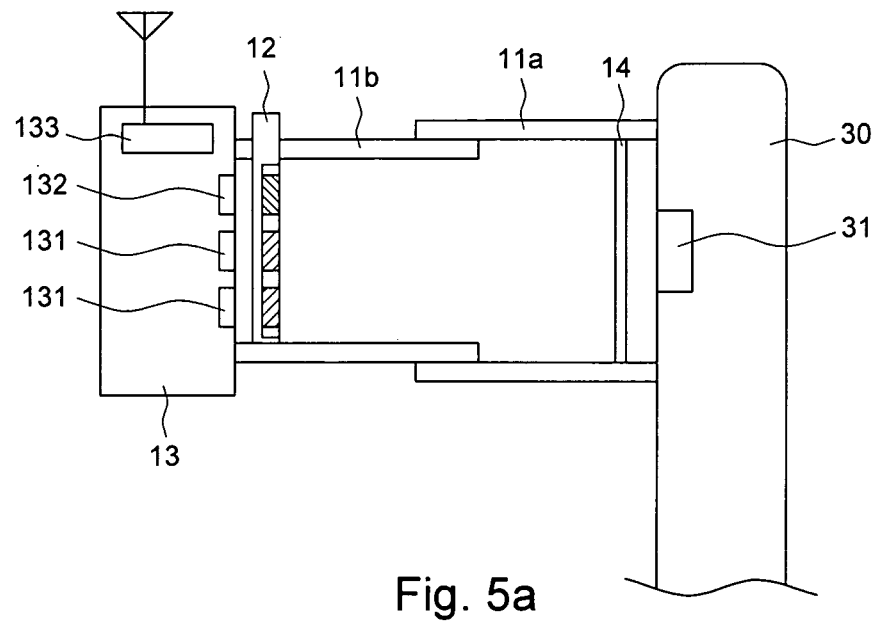
FIGS. 5a and 5b are schematic diagrams schematically illustrate further another embodiment of a portable fluorescence analysis system according to the present invention.
Figure 5B:
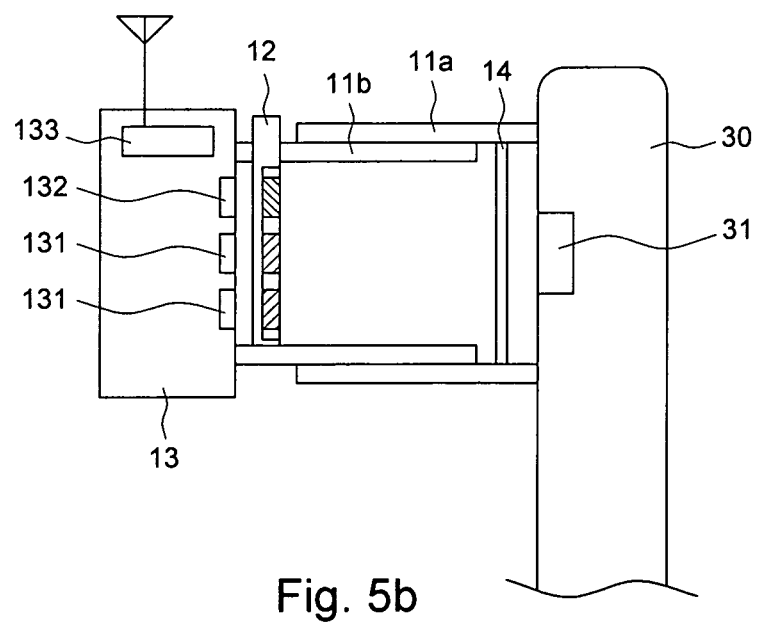

In one embodiment, the sleeve 11 comprises a focus adjusting mechanism to adjust the distance between the fluorescence strip 20 and the image capturing module 31. Referring to FIGS. 3 and 4, for example, the sleeve 11 provides a guide rail (not shown) parallel to the direction of the light axis of the image capturing module 31, and the fixing member 12 is movable along the guide rail. Under this arrangement, the fixing member 12 is movable along the direction of the light axis of the image capturing module 31 so as to adjust the distance between the fluorescence strip 20 and the image capturing module 31. In another embodiment, as shown in FIGS. 5a and 5b, the sleeve comprises a plurality of sleeves 11a and 11b which are connected with each other in a sleeve type. Under this arrangement, the sleeves 11a and 11b are slidable relative to each other so as to adjust the distance between the fluorescence strip 20 and the image capturing module 31. Based on the above-mentioned arrangements, when the image capturing module 31 is set in a fixed-focus state, a better image quality is obtained by adjusting the focus adjusting mechanism of the sleeve to adjust the focus. Alternatively, through a user manually adjusting the focus of the image capturing module 31 via the user interface of the mobile Internet device 30, and through the assistance of the focus pattern 23 of the fluorescence strip 20 for the user to measure a proper focus, a fluorescence image in focus is obtained.

To summarize the foregoing descriptions, the portable fluorescence analysis system of the present invention is configured to install the fluorescence excitation device on the mobile Internet device and perform relevant analyses by utilizing the image capturing module built into the mobile Internet device in order to capture the fluorescence image of the fluorescence strip. In other words, the portable fluorescence analysis system of the present invention is adapted to perform a fluorescence test without the need for any expensive or complex optical instrument. Therefore, the portable fluorescence analysis system of the present invention costs far below the conventional fluorescence analysis system and having a benefit of being applied to the field of the point of care testing.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A portable fluorescence analysis system comprising:
  a fluorescence strip comprising at least one detecting area;
  a fluorescence excitation device comprising:
    a non-transparent housing having a first opening and a second opening opposite to the first opening, wherein the fluorescence strip is arranged in the non-transparent housing; and
    an excitation light source module arranged to provide an exciting light towards the second opening for irradiating on the detecting area so as to excite the fluorescence strip to generate a fluorescent light, wherein the excitation light source module comprises a wireless communication unit so that the excitation light source module is able to be controlled wirelessly;

an image capturing module capturing a fluorescence image of the detecting area via the first opening.

2. The portable fluorescence analysis system according to claim 1, wherein the exciting light provided from the excitation light source module is transferred to the detecting area of the fluorescence strip via the second opening, and the fluorescent light from the fluorescence strip is received by the image capturing module via the first opening.

3. The portable fluorescence analysis system according to claim 2, wherein the excitation light source module is disposed adjacent to the second opening and the image capturing module is disposed adjacent to the first opening.

4. The portable fluorescence analysis system according to claim 3, wherein the excitation light source module is arranged opposite to the image capturing module, so that the fluorescence strip is arranged between the excitation light source module and the image capturing module.

5. The portable fluorescence analysis system according to claim 2, wherein the fluorescence excitation device comprises a filter, the filter is arranged to the side of the first opening of the non-transparent housing for filtering out at least one of the exciting light and the fluorescent light excluding a specific wavelength range of the fluorescent light.

6. The portable fluorescence analysis system according to claim 2, wherein the interior surface of the non-transparent housing has a light absorbing layer for absorbing at least one of the exciting light and the fluorescent light.

7. The portable fluorescence analysis system according to claim 2, wherein the excitation light source module further provides a reference light, the fluorescence strip has a hole corresponding to the reference light so as to provide the image capturing module to capture the fluorescence image in a proper exposure value based on the intensity of the reference light, and the center wavelength of the reference light is different from the center wavelength of the exciting light.

8. The portable fluorescence analysis system according to claim 2, wherein the non-transparent housing comprises a focus adjusting mechanism for adjusting a distance between the fluorescence strip and the image capturing module.

9. The portable fluorescence analysis system according to claim 2, wherein the image capturing module is set in a fixed-focus state to catch the fluorescence image in focus, or a focus of the image capturing module is set by a user to catch the fluorescence image in focus.

10. The portable fluorescence analysis system according to claim 2, further comprising a mobile Internet device wherein the image capturing module is integrated in the mobile Internet device.

11. The portable fluorescence analysis system according to claim 10, wherein the excitation light source module comprises a plurality of LEDs, the fluorescence strip comprises a plurality of detecting areas, and each one of the plurality detecting areas is corresponding to at least one of the plurality of LEDs.

12. The portable fluorescence analysis system according to claim 11, wherein the wireless communication unit is a Bluetooth module, which is adapted to wirelessly communicate with the mobile Internet device so as to selectively activate at least one of the plurality of LEDs through the mobile Internet device.

13. The portable fluorescence analysis system according to claim 10, wherein the wireless communication unit is a Bluetooth module, which is adapted to wirelessly communicate with the mobile Internet device so as to adjust the intensity of the exciting light of the excitation light source module through the mobile Internet device.

14. The portable fluorescence analysis system according to claim 10, wherein the wireless communication unit is a Bluetooth module which is adapted to wirelessly communicate with the mobile Internet device so as to wirelessly control the excitation light source module through the mobile Internet device.

15. The portable fluorescence analysis system according to claim 10, wherein the detecting area comprising a fluorescence probe for detecting an analyte within a specimen, and the portable fluorescence analysis system further comprises a processing module for analyzing a fluorescence intensity of the fluorescence image to estimate a content of the analyte.

16. The portable fluorescence analysis system according to claim 15, wherein the processing module is integrated in the mobile Internet device so that the fluorescence image is analyzed by the mobile Internet device and the content of the analyte is estimated.

17. The portable fluorescence analysis system according to claim 15, wherein the processing module is integrated in a host so that the fluorescence image is analyzed by transferring to the host via intranet and the content of the analyte is estimated.

18. The portable fluorescence analysis system according to claim 15, wherein the fluorescence intensity of the fluorescence image within a specific wavelength range is analyzed to estimate the content of the analyte.

19. A fluorescence excitation device, for accommodating a fluorescence strip and assembling with an imaging capturing module, wherein the fluorescence strip comprises at least one detecting area, the fluorescence excitation device comprising:

a non-transparent housing having a first opening and a second opening opposite to the first opening, wherein the fluorescence strip is arranged in the non-transparent housing; and an excitation light source module arranged to provide an exciting light towards the second opening for irradiating on the detecting area so as to excite the fluorescence strip to generate a fluorescent light, wherein the excitation light source module comprises a wireless communication unit so that the excitation light source module is able to be controlled wirelessly;

wherein the image capturing module captures a fluorescence image of the detecting area via the first opening.

20. The fluorescence excitation device according to claim 19, wherein the exciting light provided by the excitation light source module is transferred to the detecting area of the fluorescence strip via the second opening, and the fluorescent light from the fluorescence strip is received by the image capturing module via the first opening.

21. The fluorescence excitation device according to claim 20, wherein the excitation light source module is disposed adjacent to the second opening and the image capturing module is disposed adjacent to the first opening so that the excitation light source module is arranged opposite to the image capturing module and the fluorescence strip is arranged between the excitation light source module and the image capturing module.

22. The fluorescence excitation device according to claim 20, wherein the excitation light source module is adjustable in the quantity or the intensity of the exciting light.

23. The fluorescence excitation device according to claim 20, further comprising an adapter arranged to the side of the first opening of the non-transparent housing for installing the mobile Internet device to the fluorescence excitation device.

24. The fluorescence excitation device according to claim 20, further comprising a fixing member arranged to the side of the second opening for fixing the fluorescence strip to the side of the second opening of the non-transparent housing.

25. The fluorescence excitation device according to claim 20, further comprising a filter arranged to the side of the first opening of the non-transparent housing for filtering out at least one of the exciting light and the fluorescent light excluding a specific wavelength range of the fluorescent light.

26. The fluorescence excitation device according to claim 20, wherein the interior surface of the non-transparent housing has a light absorbing layer for absorbing at least one of the exciting light and the fluorescent light.

27. The fluorescence excitation device according to claim 20, wherein the excitation light source module further provides a reference light, the fluorescence strip has a hole corresponding to the reference light so as to provide the image capturing module to capture the fluorescence image in a proper exposure value based on the intensity of the reference light, and the center wavelength of the reference light is different from the center wavelength of the exciting light.

28. The fluorescence excitation device according to claim 20, wherein the non-transparent housing comprises a focus adjusting mechanism for adjusting a distance between the fluorescence strip and the image capturing module.

29. The fluorescence excitation device according to claim 20, further comprising a mobile Internet device wherein the image capturing module is integrated in the mobile Internet device.

30. The fluorescence excitation device according to claim 29, wherein the excitation light source module comprises a plurality of LEDs and the wireless communication unit is a Bluetooth module, which is adapted to wirelessly communicate with the mobile Internet device so as to selectively activate at least one of the plurality of LEDs through the mobile Internet device.

31. The fluorescence excitation device according to claim 29, wherein the wireless communication unit is a Bluetooth module which is adapted to wirelessly communicate with the mobile Internet device so as to adjust the intensity of the exciting light of the excitation light source module through the mobile Internet device.

32. The fluorescence excitation device according to claim 29, wherein the wireless communication unit is a Bluetooth module which is adapted to wirelessly communicate with the mobile Internet device so as to wirelessly control the excitation light source module through the mobile Internet device.

33. The fluorescence excitation device according to claim 29, wherein the detecting area comprising a fluorescence probe for detecting an analyte within a specimen, and the fluorescence image is transferred to a processing module for analyzing a fluorescence intensity of the fluorescence image to estimate a content of the analyte.

34. The fluorescence excitation device according to claim 33, wherein the processing module is integrated in the mobile Internet device so that the fluorescence image is analyzed by the mobile Internet device and the content of the analyte is estimated.

35. The fluorescence excitation device according to claim 33, wherein the processing module is integrated in a host so that the fluorescence image is analyzed by transferring to the host via intranet and the content of the analyte is estimated.

* * * * *